United States Patent [19]

Siddens

[11] 4,404,148

[45] Sep. 13, 1983

[54] METHOD FOR THE PREPARATION OF DIFLUOROMETHOXYAROMATIC COMPOUNDS

[75] Inventor: Jack K. Siddens, Princeton Junction, N.J.

[73] Assignee: American Cyanamid Company, Stamford, Conn.

[21] Appl. No.: 420,164

[22] Filed: Sep. 20, 1982

[51] Int. Cl.$^3$ .................. C07C 121/75; C07C 43/225; C07C 69/712; C07C 79/35

[52] U.S. Cl. ............................ 260/465 F; 260/456 R; 260/456 P; 560/55; 560/254; 568/588; 568/649; 568/655; 568/656

[58] Field of Search ............ 260/456 R, 456 P, 465 F; 560/55, 254; 568/588, 655, 656, 649

[56] References Cited

U.S. PATENT DOCUMENTS 4,199,595  4/1980  Berkelhammer et al. .......... 424/304

Primary Examiner—Dolph H. Torrence
Attorney, Agent, or Firm—Thomas J. Monahan

[57] ABSTRACT

A method for the preparation of certain difluoromethoxyaromatic compounds which are useful intermediates for the preparation of pyrethroid pesticides. The method comprises alkylating a p-substituted phenol with excess chlorodifluoromethane at atmospheric and superatomspheric pressures in the presence of a base, acetone, benzyltriethylammonium chloride, and water.

9 Claims, No Drawings

METHOD FOR THE PREPARATION OF DIFLUOROMETHOXYAROMATIC COMPOUNDS

The invention herein described relates to a method for the preparation of certain difluoromethoxyaromatic compounds. These chemicals are convenient intermediates in the preparation of certain broad spectrum pyrethroid pesticides. The method comprises the alkylation of a p-substituted phenol with excess chlorodifluoromethane at atmospheric or superatmospheric pressures in the presence of a base, acetone, benzyltriethylammonium chloride and water.

By way of background, pesticidal pyrethroids, the preparation of which conveniently involves certain of the difluoromethoxyaromatic compounds of the present invention, are disclosed and claimed in U.S. Pat. No. 4,199,595. This patent is incorporated herein by way of reference. Pyrethroid pesticides are valuable and highly effective chemicals for the control of various insects and other pests, particularly those which cause significant economic damage to field crops and livestock. Some of the pyrethroids which are described in the above-referenced patent, and prepared using intermediates of the present invention, are broad spectrum pesticides. As such they are highly effective as contact and stomach poisons for ixodidae ticks and for a wide variety of insects, particularly Dipterous, Lepidopterous, Coleopterous and Homopterous insects. They are unusual among pyrethroids in that they exhibit extended residual insecticidal activity on plant tissue. These pyrethroids are effective for the control of ixodidae and the protection of animals against attack by these organisms when administered to animals orally or parenterally or applied thereto as a topical insecticidal or acaricidal formulation.

In light of the foregoing discussion of the desirability of obtaining pyrethroid pesticides for the control of noxious pests, it is desirable to obtain the chemical intermediates which are involved in the synthesis of these products. Accordingly, an object of this invention is to provide a method for the preparation of certain difluoromethoxyaromatic compounds which can be used as intermediates in the preparation of pyrethroid pesticides. This object is manifest in the following description and particularly delineated in the appended claims.

A method for the preparation of certain difluoromethoxyaromatic compounds has been unexpectedly discovered. Such difluoromethoxyaromatic compounds are represented by structural formula-(I):

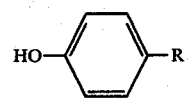
(I)

wherein R is selected from $C_1$-$C_3$ alkyl, halogen, nitro, or the moiety

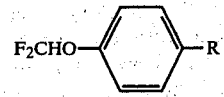

$R_1$ is —CN, —COOR$_2$, OH or OR$_3$; $R_2$ is $C_1$-$C_3$ alkyl; $R_3$ is tosyl, mesyl or $C_2$-$C_4$ alkanoyl.

A preferred group of compounds of formula-(I) may be graphically represented by structural formula-(Ia) below:

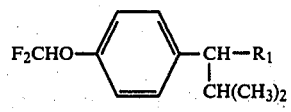
(Ia)

wherein $R_1$ is as hereinabove defined.

Another, more preferred group of compounds may be represented by formula-(Ib) below:

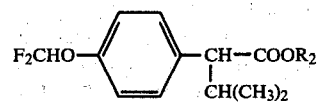
(Ib)

wherein $R_2$ is $CH_3$ or $C_2H_5$.

Of particular interest are the following compounds of formula-(I)

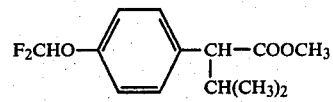

and

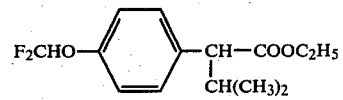

since these are valuable, and convenient intermediates for the preparation of broad spectrum pyrethroid pesticides.

Advantageously, a compound of formula-(I) may be conveniently prepared by reacting a phenol of formula-(II)

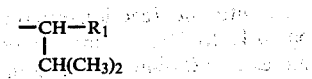
(II)

wherein R is hereinabove defined, with chlorodifluoromethane at atmospheric or superatmospheric pressures in the presence of a base, an inert water miscible solvent, water, and benzyltriethylammonium chloride (BTEAC) until the reaction is essentially complete and a compound of formula-(I) is obtained, as graphically illustrated below:

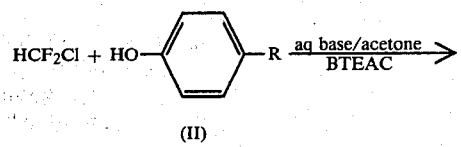

(II)

-continued

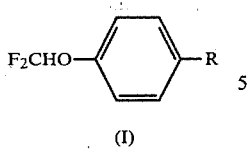

(I)

and R is as hereinabove defined. As previously stated, certain formula-(I) components are useful and valuable intermediates for the preparation of pyrethroid pesticides.

Thus, the compounds of structural formula-(Ia) may be hydrolyzed to yield the corresponding acid (i.e., structural formula-III). The acid (formula-III) is then converted to the acid chloride (i.e., structural formula-IV), and the acid chloride (formula-IV) is then reacted with a benzyl alcohol represented by structural formula-V below:

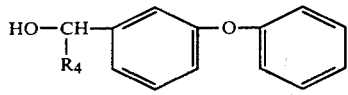

wherein $R_4$ is hydrogen or cyano, to yield the desired pyrethroid insecticide (VI). The above reaction sequence may be graphically illustrated as follows:

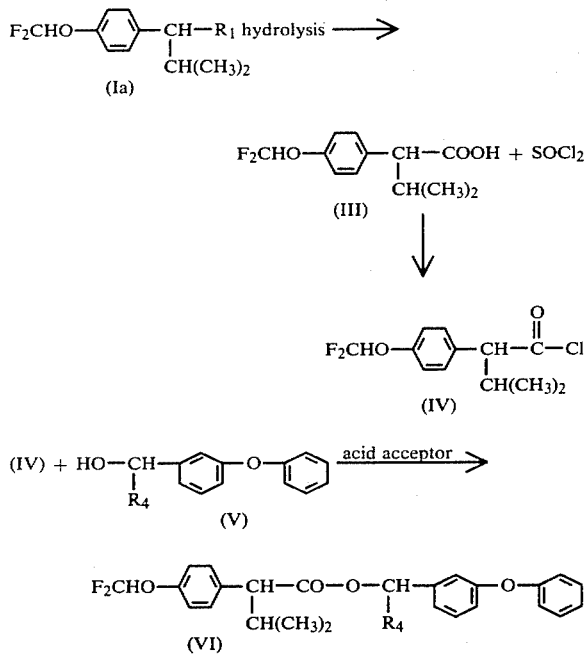

It is recognized that a chiral center is present in the formula-(III) acid at the point of attachment of the isopropyl group, and because of this conformation both d and l isomers are present. A chiral center is also present in the formula-(VI) ester. It is further recognized that when $R_4$ is cyano, a chiral center is present in the formula-(V) benzyl alcohol at the point of attachment of the $R_4$ group, allowing for an additional chiral center in the formula-(VI) pyrethroid then $R_4$ is cyano, resulting in a total of two enantiomeric pairs for the formula-(VI) pyrethroid.

Conveniently, a compound of formula-(Ia) may be prepared by the method of the present invention as follows:

One molar equivalent of a phenol of formula-(IIa)

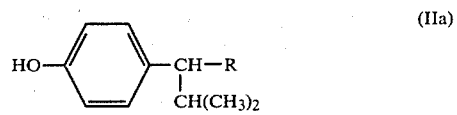

is admixed with and dissolved in a solvent mixture comprising: acetone, water used in amounts of from about 1740 to 2614 mol percent water relative to said phenol, and 10 mol percent of benzyltriethylammonium chloride relative to said phenol. In the above reaction mixture acetone is used in the range of from about 4 to 6 ml (preferably 4 ml) per gram of starting material. The system in which the reaction is to be run is then evacuated to remove any air present. Chlorodifluoromethane is then introduced under a pressure of about 0.4 to 2.5 kg cm$^{-2}$ (preferably 0.45 to 1.1 kg cm$^{-2}$). A few minutes after the start of the chlorodifluoromethane addition, one molar equivalent of aqueous sodium hydroxide, preferably 50% aqueous sodium hydroxide, is added quickly resulting in a mild exotherm. The pressure, under which the chlorodifluoromethane is added, is readjusted if necessary to about 1.0 to 1.1 kg cm$^{-2}$. Over a period of about one hour a total of two to three molar equivalents (preferably three molar equivalents) of chlorodifluoromethane are added. Simultaneously with this addition, three molar equivalents of aqueous sodium hydroxide (preferably 50% concentration) are slowly added approximately over the same period of time. The reaction temperature is maintained at a range of about 20° to 40° C. (preferably 30° to 35° C.). On completion of the additions, the reaction mixture is held for an additional period of time of about 0.1 hour to about six hours, or until the reaction is essentially complete (preferably from one to two hours). At the end of the additions the amount of water added is in the range from 2611 to 3482 mol percent relative to the moles of starting material.

The thus obtained product of formula-(I) may be isolated from the reaction mixture of separating the organic phase which contains said product from the aqueous and solid phases.

The following Example further serves to illustrate the invention and are not intended to be limitative thereof.

EXAMPLE 1

Preparation of Methyl 2-[4-(difluoromethoxy)phenyl]-3-methyl butyrate

A mixture of methyl 2-(4-hydroxyphenyl)-3-methylbutyrate (0.2 to 0.3 mol), a solvent selected from acetone or a 1:1 acetone:2-propanol mixture (used at the rate of 4 ml/g of the above compound), benzyltriethylammonium chloride (BTEAC; 0 to 10 mol percent) and water (1740 to 2614 mol percent) is stirred at 30° to 35° C. in a closed system. The system is evacuated and chlorodifluoromethane (3 molar equivalents) is introduced into the reaction mixture under a pressure of from 0.45 to 1.1 kg cm$^{-2}$ over a period of about 30 minutes to 1.0 hour. About 5 minutes after the start of the chlorodifluoromethane addition, one molar equivalent of 50.6% aqueous sodium hydroxide is added all at once (causing a slight exotherm). The slow addition of three molar equivalents of 50.6% aqueous sodium hydroxide begins and is completed in about the same period of time needed to add the chlorodifluoromethane. On completion of the additions, the reaction mixture is stirred an additional 0 to 1 hour. Next, the system is evacuated to remove any unreacted chlorodifluoromethane from the reaction mixture. The organic layer is separated and is then evaporated under vacuum. The residue is dissolved in toluene. The toluene solution is washed with dilute aqueous sodium hydroxide and then with water. The solvent is then evaporated under vacuum to yield an orange liquid, the title product.

Several experiments are run by the above procedure, and the data thus obtained are summarized in Table I below. It can be clearly seen from Table I, that the combination of acetone + 10 mol percent of BTEAC affords the highest yields attained by utilizing the above procedure.

By the above procedure, but substituting ethyl 2-(4-hydroxyphenyl)-3-methylbutyrate, 2-(4-hydroxyphenyl)-3-methylbutyronitrile, 4-chlorophenol, p-cresol or 4-nitrophenol for methyl 2-(4-hydroxyphenyl)-3-methylbutyrate, 2-[4-(difluoromethoxy) phenyl]-3-methylbutyric acid ethyl ester, 4-chloro-α,α-difluoroanisole, α,α-difluoro-4-methyllanisole or α,α-4-nitroanisole can be prepared, respectively.

TABLE I

Preparation of Methyl 2-[4-(difluoromethoxy)phenyl]-3-methylbutyrate in the presence of BTEAC

| No | Mol % water added at start | Mol % water added at end | ml of acetone per g of formula (II) | BTEAC* mol percent | Product % crude | Product % purity | Product % yield |
|---|---|---|---|---|---|---|---|
| 1 | 1740 | 2611 | 4 | — | 93.16 | 82.5 | 76.9 |
| 2 | 2614 | 3482 | 4 | — | 84.26 | 85.5 | 72.0 |
| 3 | 2614 | 3482 | 4 | — | 73.28 | 85.7 | 62.8 |
| 4 | 1740 | 2611 | 4 | 10 | 97.40 | 82.8 | 80.6 |
| 5 | 2614 | 3482 | 4 | 10 | 97.13 | 82.3 | 79.9 |
| 6 | 2014 | 3482 | 4 | 10 | 96.43 | 83.4 | 80.4 |

*BTEAC = Benzyltriethylammonium chloride

What is claimed is:

1. A method for the preparation of a compound of structural formula-(I)

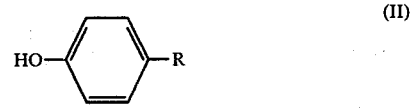
(I)

wherein R is $C_1$–$C_3$ alkyl, halogen, nitro, or the moiety

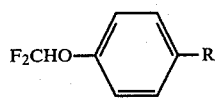

wherein $R_1$ is CN, $COOR_2$, OH or $OR_3$; $R_2$ is $C_1$–$C_3$ alkyl; $R_3$ is tosyl, mesyl or $C_2$–$C_4$ alkanoyl; comprising:

reacting one molar equivalent of a compound of structural formula-(II)

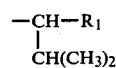
(II)

wherein R is as hereinabove defined, with two to three molar equivalents of chlorodifluoromethane added under a pressure of from about 0.4 to 2.5 kg cm$^{-2}$ over a period of time from about 30 minutes to 1.0 hour at a temperature from about 20° to 40° C., and further maintained at the above pressure and temperature ranges for about 0.1 to 6 hours, or until said reaction is essentially complete, in the presence of from about 1740 to 2614 mol percent of added water, acetone used at a rate of 4 ml per gram of the compound of formula-(II), 10 mol percent of benzyltriethylammonium chloride, and simultaneously adding to the pressurized reaction mixture an aqueous solution of four molar equivalents of an alkali metal hydroxide of sodium or potassium hydroxide over about a 1 to 4 hour period, wherein the concentration of said aqueous solution is such that on completion of the reaction the total amount of water added to the reaction mixture is from about 2614 to 3482 mol percent.

2. A method according to claim 1, wherein 3 molar equivalents of chlorodifluoromethane are added over about a 30 minute to 1.0 hour period at a pressure from about 0.4 to 1.1 kg cm$^{-2}$, at a temperature from about 30° to 35° C., and further maintained at the above pressure and temperature ranges for about 1 to 2 hours; and the alkali metal hydroxide is sodium hydroxide.

3. A method according to claim 2 wherein R is $CH_3$, Cl, $NO_2$ or

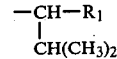

and $R_1$ is CN, $COOCH_3$, or $COOC_2H_5$.

4. A method according to claim 3, wherein said compound is methyl 2-[4-(difluoromethoxy)phenyl]-3-methylbutyrate.

5. A method according to claim 3, wherein said compound is ethyl 2-[4-(difluoromethoxy)phenyl]-3-methylbutyrate.

6. A method according to claim 3, wherein said compound is 2-[4-(difluoromethoxy)phenyl]-3-methylbutyronitrile.

7. A method according to claim 3, wherein said compound is 4-chloro-α,α-difluoroanisole.

8. A method according to claim 3, wherein said compound is 4-methyl-α,α-difluoroanisole.

9. A method according to claim 3, wherein said compound is 4-nitro-α,α-difluoroanisole.

* * * * *